United States Patent [19]

Boenko et al.

[11] Patent Number: 4,969,475
[45] Date of Patent: Nov. 13, 1990

[54] METHOD OF SURGICAL VOCAL REHABILITATION

[76] Inventors: Sergei K. Boenko, Shakhtostroitelei, 20, kv. 52; Alexandr Y. Shvartsman, Artema, 159, kv. 94, both of Donetsk, U.S.S.R.

[21] Appl. No.: 480,735

[22] Filed: Feb. 16, 1990

[30] Foreign Application Priority Data

Feb. 27, 1989 [SU] U.S.S.R. .............................. 4651605

[51] Int. Cl.⁵ ............................................. A61B 19/00
[52] U.S. Cl. .................................................. 128/898
[58] Field of Search ...................... 128/899, 898; 623/9

[56] References Cited

U.S. PATENT DOCUMENTS 4,044,402   8/1977   Edwards ................................. 623/9

FOREIGN PATENT DOCUMENTS

1405823A1   6/1988   U.S.S.R. .............................. 128/898

Primary Examiner—Ronald Frinks
Attorney, Agent, or Firm—Burgess, Ryan & Wayne

[57] ABSTRACT

A method of surgical vocal rehabilitation consists in cutting through the skin and soft tissues of the ventral neck surface, cutting the larynx, using an oblique incision, apart from the trachea with one of its cartilaginous semiring, and cutting the cartilaginous semiring off the larynx. Then the larynx is severed, the esophagus is separated from the trachea, the ventral and dorsal walls of the esophagus and trachea, respectively, are dissected to establish openings, the convex outer surface of the cartilaginous semiring is smeared with a medical adhesive, whereupon the semiring is placed onto the ventral surface of the esophagus above the opening and is fixed with sutures. Next the concave inner surface of the cartilaginous semiring round the edge of the opening in the ventral esophageal surface is smeared with a medical adhesive, and the inner surface of the semiring is stuck together with the dorsal tracheal surface. Finally, the trachea is stitched together with the skin of the ventral neck surface to establish a tracheostoma.

1 Claim, No Drawings

4,969,475

METHOD OF SURGICAL VOCAL REHABILITATION

FIELD OF THE INVENTION

The present invention relates generally to medicine and more specifically to methods of surgical vocal rehabilitation.

The present invention is successfully applicable for surgical vocal rehabilitation in patients who have sustained total laryngectomy for carcinoma.

BACKGROUND OF THE INVENTION

The proportion of laryngocarcinoma rises incessantly among all oncological diseases, having reached 8 percent in the recent years, while almost 70 percent of the patients suffer from the most wide-spread forms of the disease, that is, carcinoma stage III-IV. In view of the fact total ablation of the larynx, i.e., laryngectomy has so far been an extensively applicable mode of surgical treatment of the disease. Such a surgery though saving or prolonging patient's life, deprives him/her of voice.

People devoid of voice prove to be get out of adaption not only socially but not infrequently professionally. Thus, the problem of vocal rehabilitation can be solved by the following three methods:

logopedic (i.e., learning the so-called 'esophageal voice');
surgical.

Logopedic methods of vocal rehabilitation take much time and involve participation of specialists in diverse trades. Besides, such methods are far from being at all times capable of forming socially adequate voice as per all parameters. Speech of such patients abounds with pauses due to a scant amount of air accumulated in the esophagus. In addition, the methods in question happen to be ineffective in 12 to 18 percent of patients.

Further development of technical methods of vocal rehabilitation appears as rather promising, though it needs further improvement, since voice producing appliances feature disagreeable timbre so that patients reject them after one or two months of use.

Surgical vocal rehabilitation has gained development within the recent 20 to 25 years and is based on establishing a narrow anastomosis between the respiratory and alimentary tracts. In this case vocal rehabilitation proves to be practicable without preliminary patient's training.

One prior-art method of surgical vocal rehabilitation (SU, A, 1,405,823) is known to incorporate the following steps carried out in the sequence stated hereinbelow: incising the skin and soft tissues of the ventral neck surface; cutting the larynx off the trachea, which has a dorsal wall, a group of cartilaginous semirings, each having a convex outer surface and a concave inner surface, and a group of interannular spaces, said cartilaginous semirings alternating with said interannular spaces so as to establish conjointly the ventral wall and two lateral walls of said trachea connected to its dorsal wall; cutting off said larynx; severing the esophagus having the ventral wall and a cavity, from said trachea; cutting through said dorsal wall of said trachea to establish an opening having an edge; cutting through said ventral wall of said esophagus to form an opening having an edge situated in level with said opening in said dorsal wall of said trachea; stitching up said edges of said openings situated respectively in said ventral wall of said esophagus and in said dorsal wall of said trachea to form a bypass opening; displacing the first cartilaginous semiring of said trachea to bring it in interaction with said ventral wall of said esophagus above said opening; displacing the ventral wall of said esophagus into its said cavity at the place of interaction of said first cartilaginous semiring of said trachea with said ventral wall of said esophagus; stitching up said first cartilaginous semiring of said trachea with said ventral wall of said esophagus; stitching up said trachea with said skin of said ventral surface of said neck to establish a tracheostoma.

However, displacement of the cartilaginous semiring of the trachea along with a part of its dorsal wall into the esophageal cavity adds to the scope of surgery, which in turn, renders it more traumatic.

Moreover, application of the aforesaid method involves a great number of sutures, which sophisticates surgery.

In addition, necessity for complete severing of the cartilaginous semiring together with a part of the dorsal wall of the trachea affects adversely the wound healing conditions, which impairs postoperative management of patients.

SUMMARY OF THE INVENTION

It is an object of the present invention to provide a method of surgical vocal rehabilitation that renders surgery less traumatic. It is another object of the present invention to simplify surgery.

It is one more object of the present invention to simplify post-operative management of patients.

Said objects are accomplished due to the provision of a method for surgical vocal rehabilitation, wherein the following steps are carried out: cutting through the skin and soft tissues of the ventral neck surface, cutting the larynx, using an oblique incision, apart from the trachea, which has a dorsal wall, a group of cartilaginous semirings, each having a convex outer surface and a concave inner surface, and a group of interannular spaces, said cartilaginous semirings alternating with said interannular spaces so as to establish conjointly the ventral wall and two lateral walls of said trachea, connected to its said dorsal wall and to at least one of its said cartilaginous semirings; cutting said cartilaginous semiring off said larynx; cutting off said larynx; severing the esophagus having the ventral wall and a cavity, from said trachea; cutting through said dorsal wall of said trachea to establish an opening having an edge; cutting through said ventral wall of said esophagus to form an opening having an edge arranged at the same level with said opening in said dorsal wall of said trachea; smearing said convex outer surface of said cartilaginous semiring of said trachea with a medical adhesive; placing said cartilaginous semiring onto said ventral wall of said esophagus above said opening to establish interaction of its convex outer surface with said ventral wall of said esophagus; displacing the ventral wall of said esophagus into its said cavity at the place of interaction of said convex outer surface of said cartilaginous semiring with said ventral wall of said esophagus; fixing said cartilaginous semiring to said ventral wall of said esophagus by virtue of two catgut sutures; smearing, with a medical adhesive, said ventral wall of said esophagus round said edge of said opening and said concave inner surface of said cartilaginous semiring; sticking said dorsal wall of said trachea together with said concave surface of said cartilaginous semiring and with said ventral wall of said esophagus, accompanied by jointly fixing said edges of said respective opening in said dorsal wall of said trachea and said opening in said ventral wall of said esophagus to establish a bypass opening; stitching up said trachea with said skin of said ventral surface of said neck to establish a tracheostoma. The present invention makes it possible to reduce the scope surgery, thus rendering it less traumatic.

Besides, the present invention enables one to reduce the number of sutures, thus simplifying surgery.

The present invention makes it possible to improve conditions for wound healing, which facilitates postoperative management of patients.

Further objects and advantages of the present invention are disclosed hereinbelow in detail by consideration of a description of a specific exemplary embodiment thereof.

DETAILED DESCRIPTION OF THE INVENTION

The method of surgical vocal rehabilitation is carried onto effect as follows.

The skin and soft tissues of the ventral neck surface is incised under intubation anesthesia, the larynx is cut off the trachea along with at least one of its cartilaginous semiring, using an oblique cut, the cartilaginous semiring is cut off the larynx, the larynx is isolated from below upwards, the pharynx is slit open and cut off the muscle of the oral cavity fundus together with the hyoid bone, the ventral esophageal wall is separated from the dorsal tracheal wall, the latter is dissected, through a linear incision, as well as the ventral esophageal wall at the same level with to establish openings. Then the cartilaginous semiring is smeared, on its convex outer surface, with a medical adhesive and placed onto the ventral esophageal wall above the opening, being so oriented with its convex outer surface towards the ventral esophageal wall to, establish interaction therewith. The ventral esophageal wall is displaced into the esophageal cavity at the place of interaction with the tracheal semiring to form a projection or cornice above the opening. The edges of the cartilaginous semiring are additionally fixed with two catgut sutures. Next the tissues surrounding the opening in the ventral esophageal wall and in the concave inner surface of the semiring are smeared with a medical adhesive, whereupon the respective openings in the ventral esophageal wall and in the dorsal tracheal wall are brought in register with each other and stuck together to establish a bypass opening.

The tracheal walls are stitched together with the skin, the pharyngeal mucosa is stitched up with Lavsan (polyethyleneterephthalate) loop sutures, the wound is stiched up hermetically tight in layers, and rubber drains are inserted into it at the corners. To promote understanding of the present invention given below is the following specific example of its practical application.

Male patient, 59 was admitted to a laryngological clinic with complaints of hoarseness. Considered himself ill for about half a year when he noted hoarseness for the first time. The patient made resort to domiciliary treatment and did not have recourse to medical men.

Objective evidence: laryngoscopy detacted a tuberous tumor to occupy the middle portion of the right laryngeal half and to invade the epiglottic petiole and the interartenoid space.

A pathohistological examination revealed squamous-cell nonkeratotic carcinoma.

The larynx was cut off the trachea, under intubation anesthesia, along with one of its cartilaginous semirings, using an oblique incision, the ventral esophageal wall was separated from the dorsal tracheal wall for a depth of up to 1.5cm, the dorsal tracheal wall and the ventral esophageal wall were dissected at the same level, using a linear incision as long as 1cm, to establish respective openings.

The cartilaginous semiring was smeared with a medical adhesive on its convex outer surface and placed onto the ventral esophageal wall above the opening in such a position that the convex outer surface of the semiring should face towards the esophageal cavity, thus forming a projection or cornice above the opening. The edges of the semiring were fixed additionally with two catgut sutures, the tissues of the ventral esophageal wall were smeared with a medical adhesive round the opening, as well as those of the inner surface of the cartilaginous semiring. The esophageal mucosa wall 'pulled through' the incision in the dorsal tracheal wall, tucked up and fixed to the tracheal mucosa. Thus, the tissues were stuck together, and the opening in the dorsal tracheal wall was brought in register with that in the ventral esophageal wall to establish a bypass opening. The tracheal walls were stitched together with the skin, using loop sutures of Lavsan (polyethyleneterephthalate), the pharyngeal mucosa was stitched up, the wound was stitched up hermetically tight in layers, and rubber drains were inserted into the wound at its corners.

The postoperative period was uneventful. Alimentation of the patient up to the twelfth day was carried out through a nasoesophageal feeding tube. On the seventh day after removal of the feeding tube a sonorous voice arose in the patient with the tracheostoma closed during exhalation. No aspiration of saliva or alimentary mass through the bypass opening has been observed within a two-month follow-up period.

The present invention enables one to more efficaciously prevent saliva and alimentary mass from being aspirated in the tracheobronchial tree, which preclude the onset of inflammatory processes in the patient's respiration tracts and the lungs.

In addition, the present invention contributes to a reduced scope of surgery, which in turn curtails the operating time.

What is claimed is:

1. A method of surgical vocal rehabilitation, comprising the following steps carried out in the order stated hereinbelow:
    cutting through the skin and soft tissues of the ventral neck surface;
    cutting the larynx, using an oblique incision, apart from the trachea, which has a dorsal wall, a group of cartilaginous semirings, each having a convex outer surface and a concave inner surface, and a group of interannular spaces, said cartilaginous semirings alternating with said interannular spaces so as to establish conjointly the ventral wall and two lateral walls of said trachea, connected to its said dorsal wall and to at least one of its cartilaginous semirings;
    cutting said cartilaginous semiring of said larynx;
    cutting off said larynx;
    severing the esophagus having the ventral wall and a cavity, from said trachea;

cutting through said dorsal wall of said trachea to establish an opening having an edge;

cutting through said ventral wall at the same level with said opening in said dorsal wall of said trachea;

smearing said convex outer surface of said cartilaginous semiring of said trachea with a medical adhesive;

placing said cartilaginous semiring onto said ventral wall of said esophagus above opening to establish interaction of its convex outer surface with said ventral wall of said esophagus;

displacing the ventral wall of said esophagus into its said cavity at the place of interaction of said convex outer surface of said cartilaginous semiring with said ventral wall of said esophagus;

fixing said cartilaginous semiring to said ventral wall of said esophagus by virtue of two catgut sutures;

smearing, with a medical adhesive, said ventral wall of said esophagus round said edge of said opening and said concave inner surface of said cartilaginous semiring;

sticking said dorsal wall of said trachea together with said concave surface of said cartilaginous semiring and with said ventral wall of said esophagus, accompanied by jointly fixing said edges of said respective opening in said dorsal wall of said trachea and said opening in said ventral wall of said esophagus to establish a bypass opening;

stitching up said trachea with said skin of said ventral surface of said neck to establish a tracheostoma.

* * * * *